United States Patent
Rostovtsev

(10) Patent No.: US 8,257,836 B2
(45) Date of Patent: Sep. 4, 2012

(54) DI-SUBSTITUTED PYRENES FOR LUMINESCENT APPLICATIONS

(75) Inventor: Vsevolod Rostovtsev, Swarthmore, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 491 days.

(21) Appl. No.: 11/961,369

(22) Filed: Dec. 20, 2007

(65) Prior Publication Data

US 2008/0166595 A1 Jul. 10, 2008

Related U.S. Application Data

(60) Provisional application No. 60/877,985, filed on Dec. 29, 2006.

(51) Int. Cl.
*H01L 51/54* (2006.01)

(52) U.S. Cl. ......... 428/690; 428/917; 313/504; 313/506

(58) Field of Classification Search .................. None
See application file for complete search history.

(56) References Cited

U.S. PATENT DOCUMENTS

| | | | |
|---|---|---|---|
| 5,247,190 A | 9/1993 | Friend et al. | |
| 5,408,109 A | 4/1995 | Heeger et al. | |
| 6,852,429 B1 | 2/2005 | Li et al. | |
| 6,875,524 B2 | 4/2005 | Hatwar et al. | |
| 7,173,131 B2 | 2/2007 | Saitoh et al. | |
| 7,358,409 B2 | 4/2008 | Saitoh et al. | |
| 7,375,250 B2 | 5/2008 | Saitoh et al. | |
| 7,402,681 B2 | 7/2008 | Ong et al. | |
| 7,491,450 B2 | 2/2009 | Okinaka et al. | |
| 7,651,786 B2 * | 1/2010 | Matsuura et al. | 428/690 |
| 7,709,104 B2 | 5/2010 | Saitoh et al. | |
| 8,026,665 B2 | 9/2011 | Kim et al. | |
| 2001/0053462 A1 * | 12/2001 | Mishima | 428/690 |
| 2002/0076576 A1 | 6/2002 | Li | |
| 2003/0118866 A1 * | 6/2003 | Oh et al. | 428/690 |
| 2004/0102577 A1 | 5/2004 | Hsu et al. | |
| 2004/0106003 A1 | 6/2004 | Chen et al. | |
| 2004/0127637 A1 | 7/2004 | Hsu et al. | |
| 2004/0189190 A1 * | 9/2004 | Suzuri et al. | 313/504 |
| 2005/0031898 A1 | 2/2005 | Li et al. | |
| 2005/0158577 A1 | 7/2005 | Ishibashi et al. | |
| 2005/0184287 A1 | 8/2005 | Herron et al. | |
| 2005/0205860 A1 | 9/2005 | Hsu et al. | |
| 2006/0052641 A1 | 3/2006 | Funahashi | |
| 2006/0113528 A1 | 6/2006 | Okinaka et al. | |
| 2006/0115678 A1 * | 6/2006 | Saitoh et al. | 428/690 |
| 2006/0121312 A1 | 6/2006 | Yamada et al. | |
| 2006/0154107 A1 | 7/2006 | Kubota et al. | |

(Continued)

FOREIGN PATENT DOCUMENTS

EP 443 861 B1 7/1995

(Continued)

OTHER PUBLICATIONS

"Color." Web. Sep. 27, 2011. ,http://hyperphysics.phy-astr.gsu.edu/Hbase/vision/specol>.*

(Continued)

*Primary Examiner* — Dawn L. Garrett

(57) ABSTRACT

This invention relates to electroluminescent 4,9-di-substituted pyrenes that are useful in electroluminescent applications. It also relates to electronic devices in which the active layer includes such a pyrene composition.

1 Claim, 1 Drawing Sheet

Schematic of a light-emitting device

U.S. PATENT DOCUMENTS

| | | |
|---|---|---|
| 2006/0159838 A1 | 7/2006 | Kowalski et al. |
| 2006/0251925 A1* | 11/2006 | Hosokawa et al. ........... 428/690 |
| 2006/0267488 A1 | 11/2006 | Saitoh et al. |
| 2007/0063638 A1 | 3/2007 | Tokairin et al. |
| 2007/0114917 A1 | 5/2007 | Funahashi |
| 2007/0252511 A1* | 11/2007 | Funahashi ..................... 313/498 |
| 2007/0255076 A1 | 11/2007 | Ito et al. |
| 2007/0292713 A9 | 12/2007 | Dobbs et al. |
| 2007/0298530 A1 | 12/2007 | Feehery |
| 2008/0191614 A1 | 8/2008 | Kim et al. |
| 2008/0233433 A1 | 9/2008 | Igarashi et al. |
| 2008/0286605 A1 | 11/2008 | Takeda |
| 2009/0058279 A1 | 3/2009 | Takeda |

FOREIGN PATENT DOCUMENTS

| | | | |
|---|---|---|---|
| EP | 1437395 | A2 | 7/2004 |
| EP | 1604974 | A * | 12/2005 |
| EP | 1737277 | * | 12/2006 |
| EP | 2067766 | A1 | 6/2009 |
| EP | 2067767 | A1 | 6/2009 |
| JP | 04-175395 | * | 6/1992 |
| JP | 10-251633 | * | 9/1998 |
| JP | 2004010550 | A | 1/2004 |
| JP | 2006-140235 | * | 6/2006 |
| JP | 2006151844 | A | 6/2006 |
| JP | 2006219392 | A | 8/2006 |
| JP | 2007186449 | A | 7/2007 |
| JP | 2007208165 | A | 8/2007 |
| KR | 1020090046731 | A | 5/2009 |
| KR | 1020090086015 | A | 8/2009 |
| KR | 1020090086920 | A | 8/2009 |
| KR | 1020090093897 | A | 9/2009 |
| WO | 2005052027 | A1 | 6/2005 |
| WO | 2005115950 | A1 | 12/2005 |
| WO | 2006001333 | A1 | 1/2006 |
| WO | 2006057326 | A1 | 6/2006 |
| WO | 2006090772 | A1 | 8/2006 |
| WO | 2006112582 | | 10/2006 |
| WO | 2006137210 | A1 | 12/2006 |
| WO | 2007004364 | A1 | 1/2007 |
| WO | 2007021117 | A1 | 2/2007 |
| WO | 2007100096 | A1 | 9/2007 |
| WO | 2007105917 | A1 | 9/2007 |
| WO | 2007108457 | A1 | 9/2007 |
| WO | 2007108666 | A1 | 9/2007 |
| WO | 2007129702 | A1 | 11/2007 |
| WO | 2008149968 | A1 | 12/2008 |
| WO | 2009028902 | A2 | 3/2009 |
| WO | 2009055628 | A1 | 4/2009 |
| WO | 2010071362 | | 6/2010 |

OTHER PUBLICATIONS

Negishi et al., III.2.15 Palladium-Catalyzed Conjugate Substitution, Handbook of Organopalladium Chemistry for Organic Synthesis, 2002, vol. 1:767-789.

John Markus, Photoconductive Cell, Electronics and Nucleonics Dictionary, 1966, p. 470 & 476.

Y. Wang, Photoconductive Polymers, Kirk-Othmer Encyclopedia of Chemical Technology, 4th Edition, 1996, vol. 18:837-860.

Gustafsson et al., Flexible Light-Emitting Diodes Made From Soluble Conducting Polymers, Nature, 1992, vol. 357:477-479.

Maeda et al., "Alkynylpyrenes as Improved Pyrene-Based Biomolecular Probes with the Advantages of High Fluorescence Quantum Yields and Long Absorption/Emission Wavelengths," Chemisty—A European Journal (2006), 12(3), pp. 824-831.

March, Aromatization of Six-Membered Rings, Advanced Organic Chemistry, Wiley-Interscience (1992), 4th Ed., pp. 1162-1164.

Minabe et al., "Electrophilic Substitution of Monosubstituted Pyrenes," Bulletin of the Chemical Society of Japan (1994), 67(1), pp. 172-179.

Norman et al., The Reactions of Pyrene with Free Radicals and with Sodium, Journal of the Chemical Society, 1958, pp. 175-179.

Sheldon et al., "The Mechanism of the Collision-induced Loss of Methane from the Trimethylsilyl Negative Ion," Perkin Transaction II: Organic and Bio-Organic Chemistry, Journal of the Chemical Society (1988), (7), pp. 1263-1268.

PCT International Search Report for International Application No. PCT/US2009/068922; Hyun Shik Oh, Authorized Officer; Oct. 20, 2010.

* cited by examiner

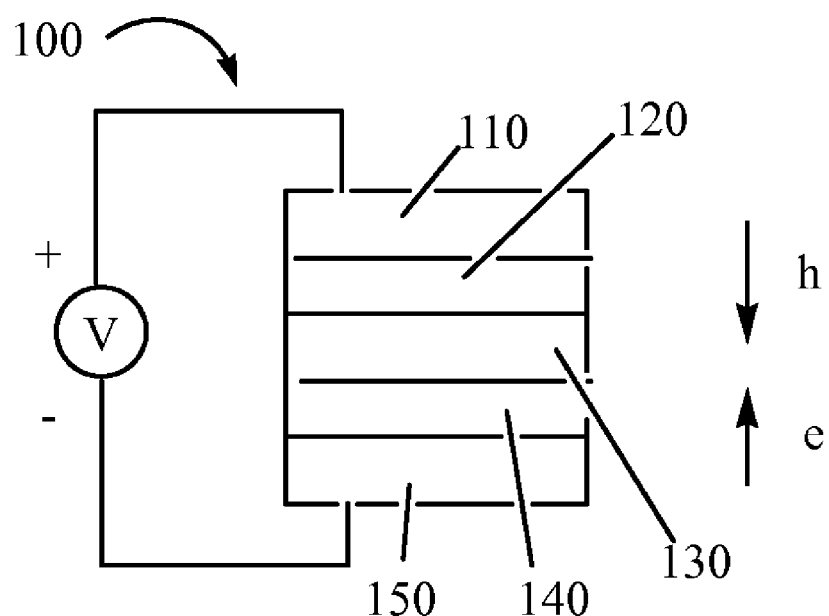
Schematic of a light-emitting device

US 8,257,836 B2

DI-SUBSTITUTED PYRENES FOR LUMINESCENT APPLICATIONS

RELATED APPLICATION DATA

This application claims priority under 35 U.S.C. §119(e) from U.S. Provisional Application No. 60/877,985 filed on Dec. 29, 2006, which is incorporated by reference herein in its entirety.

BACKGROUND

1. Field of the Disclosure

This invention relates to electroluminescent 4,9-disubstituted pyrenes. It also relates to electronic devices in which the active layer includes such a pyrene composition.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861.

However, there is a continuing need for electroluminescent compounds, especially compounds that are blue-emitting.

SUMMARY

There is provided a composition having Formula I:

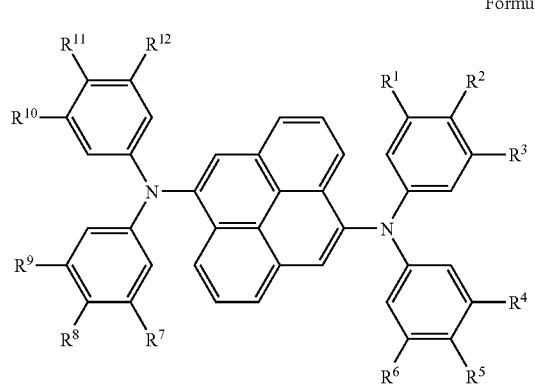

Formula I wherein each R is independently selected from the group consisting of hydrogen, fluoro, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl; with the proviso that at least one of $R^1$, $R^3$, $R^4$, $R^6$, $R^7$, $R^9$, $R^{10}$, and $R^{12}$ is selected from the group consisting of a fluoro group and a fluoroalkyl group.

There is also provided an electronic device comprising an active layer comprising the compound of Formula I.

BRIEF DESCRIPTION OF THE DRAWINGS

FIG. 1 is a schematic diagram of a light-emitting device (LED).

DEFINITION OF TERMS

As used herein, the term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81$^{st}$ Edition, 2000).

DETAILED DESCRIPTION

One aspect of the present invention is a composition of Formula I:

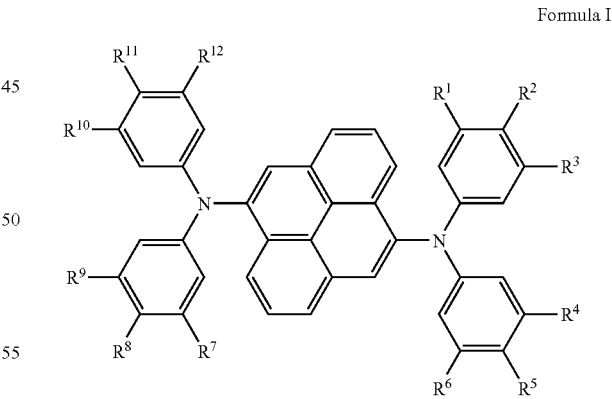

Formula I wherein each R is independently selected from the group consisting of hydrogen, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl; with the proviso that at least one of $R^1$, $R^3$, $R^4$, $R^6$, $R^7$, $R^9$, $R^{10}$, and $R^{12}$ is selected from the group consisting of a fluoro group and a fluoroalkyl group.

Suitable alkyl groups include $C_1$-$C_{20}$ substituted and unsubstituted alkyls. Suitable fluoroalkyls include $C_1$-$C_{20}$ alkyls in which one or more hydrogens have been replaced with fluorine. Fluoroalkyls include partially and fully fluorinated groups. Suitable aryls include substituted and unsubstituted phenyl and naphthyl groups. Suitable heteroaryls include substituted and unsubstituted pyridines, quinolines, isoquinolines, pyrimidines, pyrazines, pyridazines, purines, indoles, isoindoles, benzothiophenes, quinazolines, cinnolines, benzofurans, benzimidazoles, quinoxalines and inolines. Suitable diarylaminos, diarylphosphinos, and diarylphosphoryls include amino, phosphino, and phosphoryl groups, respectively, comprising two substituted or unsubstituted phenyl groups. Suitable dialkylaminos, dialkylphosphinos, and dialkylphosphoryls include amino, phosphino, and phosphoryl groups, respectively, comprising two substituted or unsubstituted $C_1$-$C_{10}$ alkyl groups. Suitable aryl(alkyl) amino groups include amino groups comprising one substituted or unsubstituted phenyl group and one substituted or unsubstituted $C_1$-$C_{10}$ alkyl group. Suitable arylthio (or arylseleno) groups include thio (or seleno) groups comprising one substituted or unsubstituted phenyl group. Suitable alkylthio (or alkylseleno) groups include thio (or seleno) groups comprising one $C_1$-$C_{10}$ substituted or unsubstituted alkyl group. Suitable aryloxy groups include oxy groups comprising one substituted or unsubstituted phenyl group. Suitable alkoxy groups include oxy groups comprising a substituted or unsubstituted $C_1$-$C_{10}$ alkyl group.

Suitable substituents for the aryl groups include halo, amino, silyl, and $C_1$-$C_{10}$ alkyl groups. Suitable substituents for the alkyl groups include amino, halo and silyl groups.

The new pyrenes can be prepared by the Suzuki coupling of the corresponding 4,9-dibromopyrene with appropriate substituents groups using standard palladium catalysts. Typical Suzuki reactions are described by Negishi, et al., Palladium-catalyzed cross-coupling substitution. Handbook of Organopalladium Chemistry for Organic Synthesis (2002), 1 767-789. Suitable reaction times are from about 5-100 hours. Suitable temperatures are from about 24-140° C. Suitable solvents include dioxanes, toluene, and tetrahydrofuran. Isolation and purification of the di-substituted pyrene product can be accomplished by techniques such as extraction, chromatography, crystallization, sublimation, used alone or in combination.

The pyrene compounds described herein are neutral and non-ionic, and can be sublimed intact. Thin films of these materials obtained via vacuum deposition exhibit good to excellent electroluminescent properties and blue emission.

Electronic Device

A generic organic light emitting diode (OLED) consists of several thin-film layers: (1) a transparent anode, usually indium tin oxide (ITO) on glass, (2) a hole transport material, (3) a luminescent material, (4) an electron transport material, and (5) a metallic cathode (e.g. Al, Al/LiF, or a low work-function metal alloy). The electrons and holes are injected from the cathode and anode into the device, and are then induced to recombine within the luminescent layer by the use of hole-transport and electron-transport layers. Recombination of electrons and holes generates an excited state of the molecular species that emits light.

A typical OLED device structure is shown in FIG. 1. The device 100 has an anode layer 110 and a cathode layer 150. Adjacent to the anode is a layer 120 comprising hole transport material. Adjacent to the cathode is a layer 140 comprising an electron transport/anti-quenching material. Between the hole transport layer and the electron transport/anti-quenching layer is the photoactive layer 130. As an option, devices frequently have a hole injection layer 115 (not shown) between the anode and the hole transport layer, and may have another electron transport layer 145 (not shown), between the cathode the first electron transport layer. Layers 115, 120, 130, 140, and 145 are individually and collectively referred to as the active layers.

Depending upon the application of the device 100, the photoactive layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, Electronics and Nucleonics Dictionary, 470 and 476 (McGraw-Hill, Inc. 1966).

Triarylmethane derivatives are particularly useful as the hole transport layer 120, and as a charge conducting host in the photoactive layer, 130. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate.

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

Examples of the photoactive layer 130 include all known electroluminescent materials. These electroluminescent complexes can be used alone, or doped into charge-carrying hosts, as noted above. The di-substituted pyrenes of Formula I, in addition to being useful as emissive dopants in the photoactive layer, can also act as charge carrying hosts for other emissive dopants in the photoactive layer 130.

Examples of additional electron transport materials which can be used in layer 140 include metal chelated oxinoid compounds, such as tris(8-hydroxyquinolato)aluminum ($Alq_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4- fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, the hole transport layer 120, the electron transport layers 140 and 160, or cathode layer 150, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layers 140 and 160, 50-2000 Å, preferably 100-1000 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses will depend on the exact nature of the materials used.

The present invention also relates to an electronic device comprising at least one photoactive layer positioned between two electrical contact layers, wherein the at least one layer of the device includes the di-substituted pyrene of Formula I. Devices frequently have additional hole transport and electron transport layers.

The pyrene compounds described herein are particularly useful as the photoactive material in layer 130, or as electron transport material in layer 140. Preferably the pyrene compounds are used as the light-emitting material in diodes. Additional materials can be present in the emitting layer with the di-substituted pyrene. For example, a fluorescent dye can be present to alter the color of emission. A diluent can also be added and such diluent can be a charge transport material or an inert matrix. A diluent can comprise polymeric materials, small molecule or mixtures thereof. A diluent can act as a processing aid, can improve the physical or electrical properties of films containing the di-substituted pyrene. Non-limiting examples of suitable polymeric materials include poly(N-vinyl carbazole), polyfluorene, and polysilane. Non-limiting examples of suitable small molecules include 4,4'-N,N'-dicarbazole biphenyl, bis(2-methyl-8-quinolinolato)(para-phenyl-phenolato)aluminum(III) (BAlQ); and tertiary aromatic amines. When a diluent is used, the pyrene is generally present in a small amount. In one embodiment, the pyrene of Formula I is less than 20% by weight, based on the total weight of the layer. In another embodiment, the di-substituted pyrene of Formula I is less than 10% by weight, based on the total weight of the layer.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the di-substituted pyrenes described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The pyrenes of the invention often are phosphorescent and photoluminescent and can be useful in applications other than OLEDs, such as oxygen sensitive indicators and as phosphorescent indicators in bioassays.

EXAMPLES

The following examples illustrate certain features and advantages of the present invention. They are intended to be illustrative of the invention, but not limiting. All percentages are by weight, unless otherwise indicated.

Tris(dibenzylideneacetone) dipalladium ($Pd_2(dba)_3$) was purchased from Alfa-Aesar (Ward Hill, Mass.).

All other reagents were purchased and used as received from Sigma-Aldrich Co. (Milwaukee, Wis.), unless otherwise indicated.

Example 1

This example illustrates the preparation of 4,9-(N,N'-bis(4-isopropylphenyl)-N,N'-bis(3,5-bis(trifluoromethyl)phenyl)) pyrenediamine In a drybox, 4,9-dibromopyrene (0.644 g, 1.79 mmol) was placed into a thick-walled glass tube, together with $Pd_2(dba)_3$ (0.172 g, 0.19 mmol)) and tri-tert-butylphosphine (0.0762 g, 0.38 mmol). N-(4-iso-Propylphenyl)-bis-3,5-trifluoromethylaniline (1.3078 g, 3.77 mmol) was dissolved in 10 ml of dry toluene and added to the reaction vessel. Sodium tert-butoxide (0.4343 g, 4.52 mmol) was added last and was followed by 20 ml of dry toluene. Glass tube was sealed, taken out of the drybox and placed into a 105° C. oil bath. In a matter of minutes the color of the reaction mixture changed from dark red to dark yellow to yellow-brown. Reaction mixture was kept in the oil bath overnight (18 h). Reaction progress was monitored by TLC. Once complete, reaction mixture was cooled to room temperature, diluted with 100 ml of $CH_2Cl_2$ and filtered through Celite. Volatiles were removed under reduced pressure and the resulting solid was purified by column chromatography on silica gel twice (2% CH$_2$Cl$_2$ in hexanes). Yield 160 mg (10%).

Color coordinates: x 0.151, y 0.055

PL (toluene solution): 440 nm $^1$H NMR (CDCl$_3$, ppm): 1.24 (d, 12H, $^3J_{HH}$=6.9 Hz), 2.90 (sept, 2H, $^3J_{HH}$=6.9 Hz), 7.25 (AB m, 8H), 7.35 (br s, 2H), 7.40 (br s, 4H), 7.95 (app t, 2H), 8.06 (s, 2H), 8.17 (app d, 2H), 8.27 (app d, 2H) $^{19}$F NMR (CDCl$_3$, ppm): −63.9 (s). Found: % C, 66.95; % H, 4.70; % N, 2.84. Calcd. for C$_{50}$H$_{36}$F$_{12}$N$_2$: % C, 67.26; % H, 4.06; % N, 3.14.

X-ray diffraction confirmed the structure

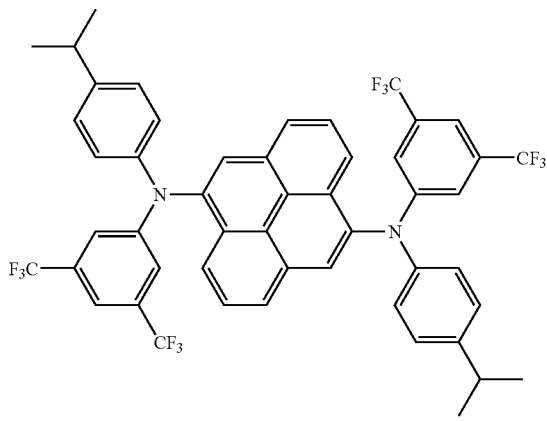

Example 2

This example illustrates the preparation of 4,9-(N,N'-bis (4-isopropylphenyl)-N,N'-bis(3-trifluoromethyl phenyl)) pyrenediamine (B961, V.

The experimental procedure described in Example 1 was used to couple 4,9-dibromopyrene and N-(4-iso-propylphenyl)-3-trifluoromethylaniline. Yield 0.94 g (73%).

Color coordinates: x 0.149, y 0.095

PL (toluene solution): 454 nm $^1$H NMR (CD$_2$Cl$_2$): δ 1.15 (d, 12H, $^3J_{HH}$=6.9 Hz), 2.79 (sept, 2H, $^3J_{HH}$=6.9 Hz), 7.04-7.25 (m, 16H), 7.81 (app t, 2H), 7.91 (s, 2H), 8.01 (app d, 2H), 8.18 (app d, 2H). $^{19}$F NMR (CD$_2$Cl$_2$, ppm): δ−63.5 (s)

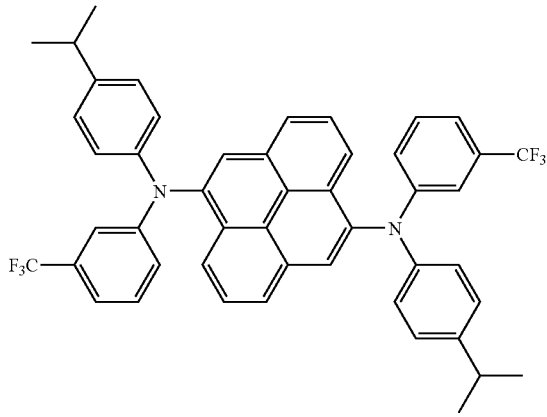

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. An organic electronic device comprising:
   a. a first electrical contact layer;
   b. a photoactive layer comprising a compound of Formula I:

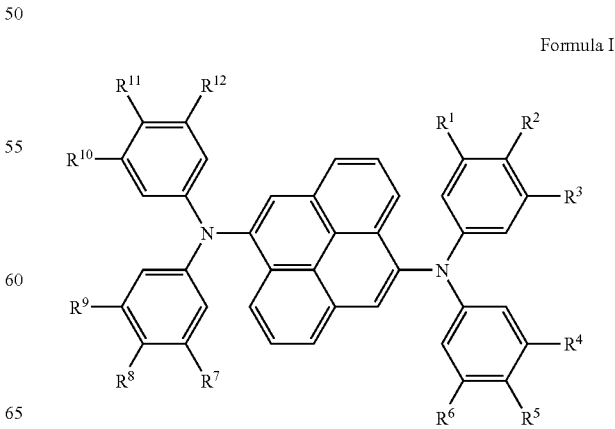

Formula I wherein each one of $R^1$ through $R^{12}$ is independently selected from the group consisting of hydrogen, fluoro alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl; with the proviso that at least one of $R^1$, $R^3$, $R^4$, $R^6$, $R^7$, $R^9$, $R^{10}$, and $R^{12}$ is selected from the group consisting of a fluoro group and a fluoroalkyl group; and c. a second electrical contact layer;

wherein the compound of Formula I is an emissive dopant with blue emission.

* * * * *